(12) United States Patent
Zanzottera et al.

(10) Patent No.: US 9,932,499 B2
(45) Date of Patent: Apr. 3, 2018

(54) UV-CURABLE COMPOSITION AND PRESSURE SENSITIVE ADHESIVE HAVING BREATHABILITY DERIVED THEREFROM, AS WELL AS METHOD FOR MANUFACTURING THE SAME

(71) Applicant: ICAP-SIRA S.p.A., Parabiago (IT)

(72) Inventors: Giorgio Zanzottera, Parabiago (IT); Robert Henry Mayan, Parabiago (IT)

(73) Assignee: ICAP-SIRA S.p.A., Parabiago (MI) (IT)

( * ) Notice: Subject to any disclaimer, the term of this patent is extended or adjusted under 35 U.S.C. 154(b) by 94 days.

(21) Appl. No.: 14/554,135

(22) Filed: Nov. 26, 2014

(65) Prior Publication Data
US 2015/0152297 A1   Jun. 4, 2015

(30) Foreign Application Priority Data
Nov. 29, 2013   (EP) .................................... 13195047

(51) Int. Cl.
| | |
|---|---|
| C09J 7/02 | (2006.01) |
| C08F 220/18 | (2006.01) |
| A61L 15/24 | (2006.01) |
| A61L 15/58 | (2006.01) |
| C09J 4/00 | (2006.01) |

(52) U.S. Cl.
CPC ............. *C09J 7/0217* (2013.01); *A61L 15/24* (2013.01); *A61L 15/58* (2013.01); *C08F 220/18* (2013.01); *C09J 4/00* (2013.01); *C09J 2201/606* (2013.01); *C09J 2201/61* (2013.01); *C09J 2433/00* (2013.01); *Y10T 428/2809* (2015.01)

(58) Field of Classification Search
CPC ......... C08F 220/18; C08F 133/08; C09J 4/00; C09J 7/0217; C09J 2201/606; C09J 2201/61; C09J 2243/00; A61L 15/24; A61L 15/58
USPC ............................................................ 522/35
See application file for complete search history.

(56) References Cited

U.S. PATENT DOCUMENTS

| | | | | |
|---|---|---|---|---|
| 4,155,157 A * | 5/1979 | Gersbacher | .......... | B23K 1/0012 228/44.3 |
| 4,224,454 A * | 9/1980 | McDowell | ................ | C08F 2/50 522/10 |
| 4,737,559 A * | 4/1988 | Kellen | .................... | A61L 15/58 522/154 |
| 5,506,279 A * | 4/1996 | Babu | ..................... | C07C 233/49 522/34 |
| 5,849,325 A | 12/1998 | Heinecke et al. | | |
| 5,902,836 A * | 5/1999 | Bennett | .................... | C08F 2/48 522/114 |
| 6,171,985 B1 * | 1/2001 | Joseph | .................. | A61L 15/585 428/316.6 |
| 6,586,491 B2 * | 7/2003 | Husemann | ........... | C08F 220/18 428/343 |
| 6,720,399 B2 * | 4/2004 | Husemann | ........... | C08F 220/12 428/355 R |
| 6,831,114 B2 * | 12/2004 | Husemann | ............... | C08F 8/00 522/129 |
| 6,903,151 B2 | 6/2005 | Lucast et al. | | |
| 7,144,928 B2 * | 12/2006 | Husemann | ........... | C09J 133/02 428/346 |
| 7,304,119 B2 * | 12/2007 | Balzer | ...................... | C08F 2/50 526/317.1 |
| 2004/0048944 A1 * | 3/2004 | Cartellieri | ................ | C08F 8/00 522/113 |
| 2005/0192370 A1 | 9/2005 | Fansler et al. | | |
| 2007/0106011 A1 * | 5/2007 | Husemann | ........... | C08F 220/12 524/555 |
| 2008/0233348 A1 * | 9/2008 | Ishiwatari | ............. | C09J 7/0207 428/134 |

(Continued)

FOREIGN PATENT DOCUMENTS

| | | |
|---|---|---|
| DE | 101 50 486 A1 | 4/2003 |
| EP | 13195047.9 | 3/2014 |

(Continued)

OTHER PUBLICATIONS

European Search Report dated Mar. 21, 2014 for Application No. EP 13195047.9.

(Continued)

*Primary Examiner* — Sanza McClendon
(74) *Attorney, Agent, or Firm* — Wolf, Greenfield & Sacks, P.C.

(57) ABSTRACT

The present invention relates to a polymerizable composition, comprising a polymerizable monomer of formula (I), a copolymerizable UV-initiator, at least one copolymerizable (meth)acrylic monomer:

$$R^1-(OCH_2CH_2)n\text{-L-OC(O)}-CR^2=CH_2 \qquad \text{Formula (I)}$$

wherein $R^1$ is hydrogen or a $C_1$-$C_6$ alkyl group, n is an integer from 1 to 100, L is a single bond or a divalent linking group, preferably a single bond or a $C_{1-6}$ alkylene group, and $R^2$ is hydrogen or a $CH_3$ group; and optionally (d) at least one copolymerizable non-acrylate monomer;

wherein the amount of the polymerizable monomer of formula (I) is between 2.5 and 40% by weight of the total of all polymerizable monomers (a), (b), (c) and (d).

The invention also relates to a random copolymer obtained by reacting the polymerizable composition, a crosslinked product of the random copolymer and an adhesive composite material comprising the random copolymer or the crosslinked product on a substrate.

12 Claims, No Drawings

(56) References Cited

U.S. PATENT DOCUMENTS

2011/0319514 A1* 12/2011 Breiner .................. C04B 41/009
522/35

FOREIGN PATENT DOCUMENTS

| EP | 13195047.9 | 5/2016 |
|----|------------|--------|
| GB | 898065 | 6/1962 |
| WO | WO 84/03837 A1 | 10/1984 |
| WO | WO 03/070792 A1 | 8/2003 |
| WO | WO 2010/107390 | 9/2010 |

OTHER PUBLICATIONS

Notice of Opposition filed May 4, 2016 for European Patent No. EP 2 878 606 (Application No. 13195047.9). Filed by Opponent Henkel AG & Co. KGaA.

Gan et al., Microporous polymeric composites from bicontinuous microemulsion polymerization using a polymerizable nonionic surfactant. Polymer. 1997;38(10):5339-45. Abstract only.

Schmitt, Room Temperature Curable Systems. Applied Technology Monomers. European Coatings Show. Mar. 31, 2009. 15 pages.

Gan et al., Microporous polymeric composites from bicontinuous microemulsion polymerization using a polymerizable nonionic surfactant. Polymer. 1997;38(10):5339-45.

* cited by examiner

UV-CURABLE COMPOSITION AND PRESSURE SENSITIVE ADHESIVE HAVING BREATHABILITY DERIVED THEREFROM, AS WELL AS METHOD FOR MANUFACTURING THE SAME

CROSS REFERENCE TO RELATED APPLICATIONS

This application claims the priority benefit of European Patent Application No. 13195047.9, filed Nov. 29, 2013, incorporated herein by reference.

FIELD OF THE INVENTION

The present invention generally relates to the field of pressure-sensitive adhesives, in particular hotmelt adhesives. In particular, the present invention relates to UV curable compositions, pressure sensitive adhesive compositions and cross-linked products formed therefrom, composite materials comprising a layer of the pressure sensitive adhesive, as well as methods for the manufacture therefor.

BACKGROUND OF THE INVENTION

Pressure-sensitive adhesives (PSA) are used in a variety of applications due to their versatility. For instance, pressure-sensitive adhesives are used for the manufacture of adhesive tapes for packaging or office purposes, yet are also used in the field of medical tapes, plasters, wound or surgical dressings, athletic tapes, or tapes or tabs used in adhering medical devices, such as sensors, electrodes, etc. to the human skin. The later applications are possible since pressure-sensitive adhesives not only adhere to inorganic materials, such as a glass, but also to organic materials, e.g. skin. Further, pressure-sensitive adhesives are known that adhere to wet or moist surfaces, known as "wet-stick" adhesives.

Pressure-sensitive adhesives are known in the art, and usually a high peel strength (adhesion strength) can be obtained. In some applications it is however necessary that the pressure-sensitive adhesive is breathable, i.e. permeable to a certain degree to water vapor. This is particularly important for applications in the medical field, such as for medical tapes, wound dressing or plasters, where a breathable pressure-sensitive adhesive allows for the transportation of moisture from the skin of a wearer, thereby contributing to the wearer's comfort and avoiding or reducing skin irritation. Also in the field of sport tapes such characteristics may be desirable. Conventional pressure-sensitive adhesives are typically not breathable, i.e. have a water vapour transmission rate of 200 $g/m^2*24$ h or less at a thickness corresponding to a coating weight of 30 $g/m^2$ when tested according to the method employed in the Examples of the present invention (UNI-4818-26).

Typically, pressure-sensitive adhesives are based on acrylates, in particular (meth)acrylates. (Meth)acrylates are known for their optical clarity and inherently tacky nature, yet are also chemically robust and resistant to oxidation. (Meth)acrylate-based pressure-sensitive adhesives are typically blends or copolymers prepared from monomers such as (meth)acrylic acid, and esters thereof with non-tertiary alcohols. These monomers are typically copolymerized radically in a solution thereof in an organic solvent. The radical polymerization is typically initiated by including a radical polymerization initiator that decomposes in response to an external stimulus, such as heat, to thereby form radicals that initiate the polymerization reaction. In view of the exothermic nature of the reaction, the polymerization is typically performed by including none or only a small amount of the monomers and the thermal polymerization initiator in a solvent and heating the reaction mixture to thereby form radicals that are capable of initiating the polymerization reaction, and then adding the copolymerizable monomers over time (typically several hours). This allows avoiding a too vigorous reaction. Additionally, modifying the reaction conditions, such the amount of initiator and the monomer feed rate, also allows obtaining polymers having the desired molecular weight.

Alternatively, in the prior art also other kinds of initiating radical polymerization of the monomers were employed, such as use of a compound that decomposes upon irradiation with UV light to thereby form radicals and initiate the polymerization.

Regardless of the type of polymerization initiation, the resulting polymers are then typically essentially linear molecules of high molecular weight, and the polymers have a high viscosity at low temperatures (such as room temperature). In order to process these polymers in the absence of a solvent, such as application to a backing or substrate, the polymers are then usually heated to higher temperatures, thereby reducing their viscosity. Due to their processability in a heated state, these classes of compounds are also known as hotmelt adhesives. Alternatively, the polymers may also be kept in the presence of a solvent, which lowers the viscosity of the overall mixture and which may facilitate the further processing of the polymers. These materials may then be referred to as solvent-based adhesives.

The adhesive properties and further properties of the obtained polymer are strongly influenced by the cohesive properties, the shear resistance and the viscoelastic properties of the polymer. The essentially linear polymer obtained directly after the synthesis as outlined above shows good adhesive properties, yet has only little cohesiveness and shear-resistance. In order to obtain a desired balance of properties, it is often useful to increase the cohesion and shear resistance. This can be achieved by a three-dimensional crosslinking of the essentially linear polymer obtained by the radical synthesis outlined above.

For these reasons, the polymer is typically cross-linked after its application, i.e. on the backing, for instance by further heating or by including a photoinitiator and irradiating the essentially linear polymer on the backing, thereby forming radicals that three-dimensionally crosslink the linear polymers, forming a polymer network.

While therefore a great variety of pressure-sensitive adhesive compositions are known, there still remains a need for improved pressure-sensitive adhesives that can be easily prepared and that provide breathability even in the cross-linked state. For the application in the medical field, the adhesive furthermore must not contain toxic or irritative substances.

From an industrial point of view, it is further preferred that the pressure-sensitive adhesive is a rather homogeneous material and does not cause a phase separation, as could be expected in the case of mixtures of different components. Further, the material should be processable when hot, so that it can be applied onto e.g. a backing or a substrate.

In an attempt to provide pressure-sensitive adhesives for the medical field, U.S. Pat. No. 6,903,151 suggests using an adhesive composition comprising (i) at least one copolymerized monoethylenically unsaturated (meth)acrylic acid ester monomer, wherein the homopolymer thereof has a Tg of less than 10° C., (ii) at least one copolymerized hydrophilic acidic monomer and (iii) at least one non-reactive poly(alkylene oxide)copolymer comprising at least two copolymerized alkylene oxides of which one is hydrophilic (e.g. ethylene oxide) and at least one of which is hydrophobic (e.g. propylene oxide). This adhesive therefore comprises at least three different components, which have to be prepared in advance. Further, the poly(alkylene oxide) copolymer is not reacted with or intimately bound to the other components of the adhesive composition, so that the poly(alkylene oxide)copolymer is likely to leak out from the adhesive composition and to cause a phase separation upon storage.

Compared to such blends of polymers, copolymers have the advantage of being obtainable in a one-step process (polymerization) and after that, are ready-to-use. Blends require an additional mixing step, which is adding cost and can be tedious to achieve perfect homogeneity. Further, in many cases different polymers are not perfectly miscible, causing blending problems and inhomogeneities and differences in performance and characteristics depending on mixing quality. Also, copolymers avoid issues like migration, diffusion, also to the skin, which may cause irritation or poisoning. Copolymers avoid these issues altogether.

SUMMARY OF THE INVENTION

The present invention has been made in view of the problems of the prior art. It is therefore an object of the present application to provide a breathable pressure-sensitive adhesive fulfilling one or more (preferably all) of the following properties:

1. The pressure-sensitive adhesive is easy to produce;
2. The pressure-sensitive adhesive is breathable;
3. The pressure-sensitive adhesive is non-toxic and non-irritant; and
4. The pressure-sensitive adhesive does not cause phase separation upon prolonged storage; and
5. The pressure-sensitive adhesive has high adhesion force
6. The pressure-sensitive adhesive is hot-melt processable.

These and other objects of the present invention will become more apparent in view of the following description.

In the broadest aspect, the present invention provides the following:

1. A polymerizable composition, comprising
   (a) a polymerizable monomer of formula (I),
   (b) a copolymerizable UV-initiator,
   (c) at least one copolymerizable (meth)acrylic monomer:

$$R^1—(OCH_2CH_2)_n\text{-}L\text{-}OC(O)—CR^2=CH_2 \quad \text{Formula (I):}$$

wherein $R^1$ is hydrogen or a $C_1\text{-}C_6$ alkyl group, n is an integer from 1 to 100, L is a single bond or a divalent linking group, preferably a single bond or a $C_1\text{-}C_6$ alkylene group, and $R^2$ is hydrogen or a $CH_3$ group; and
   optionally (d) at least one copolymerizable non-acrylic monomer;
   wherein the amount of the polymerizable monomer of formula (I) is between 2.5 and 40% by weight of the total of all polymerizable monomers (a), (b), (c) and (d).

2. The polymerizable composition according to item 1, which further comprises (e) a solvent selected from alcohols, ketones, ethers, aliphatic hydrocarbons, esters and mixtures thereof.

3. The polymerizable composition according to item 1 or 2, wherein the copolymerizable UV-initiator (b) is a compound having an acrylate or methacrylate moiety and a moiety that is decomposed by UV radiation to form radicals.

4. The polymerizable composition according to item 1 or 2, wherein the copolymerizable UV initiator (b) is selected from the group consisting of benzophenon(meth)acrylate, benzoin(meth)acrylate and compounds represented by formula (VI) below:

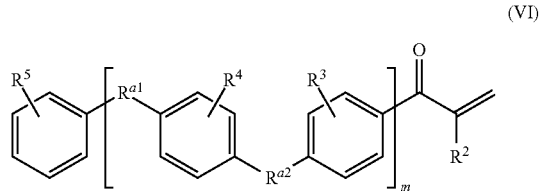

wherein $R^2$ represents a hydrogen atom or a methyl group, preferably a methyl group, $R^{a1}$ and $R^{a2}$, which may be the same or different, each represents a carbonyl group —C(O)— or an ether linkage —O—; m represents an integer from 1 to 5, preferably an integer of 1 or 2, further preferably 1; $R^3$, $R^4$ and $R^5$, which may be the same or different, each represent one or two optional substituents, which are preferably selected from $C_{1\text{-}6}$ alkyl groups, halogens (iodo, chloro, bromo or fluoro), amino groups, nitro groups, nitrile groups, and hydroxyl groups, or which may be absent ($R^3$, $R^4$ are all hydrogen), and if m is an integer of 2 or greater, the m $R^{a1}$, $R^{a2}$, $R^3$ and $R^4$ may respectively be the same or different.

5. The polymerizable composition according to any of items 1, 2, 3 and 4, wherein the at least one copolymerizable (meth)acrylic monomer (a) comprises (meth)acrylic acid, butyl (meth)acrylate and/or 2-ethylhexyl methacrylate.

6. A random copolymer obtainable by polymerizing a composition according to any of items 1 to 5.

7. A crosslinked product obtainable by irradiating the random copolymer according to item 6 with UV irradiation.

8. The crosslinked product according to claim 7, which has a water vapor transmission rate (breathability) of at least 250 g/m²*24 h according to UNI4818-26 at a coating weight of 30 g/m².

9. A composite material comprising the crosslinked product according to item 7 or item 8 on a substrate.

10. The composite material according to item 9, which is in the form of an adhesive sheet or tape, wound dressing, or plaster.

11. A method for forming a breathable adhesive composite material, comprising the steps
    i. applying a composition comprising a random copolymer according to item 6, preferably at a temperature of 120-160° C., onto a substrate; and
    ii. then irradiating the composition with UV irradiation so as to crosslink the composition.

12. Use of a composition according to any one of items 1 to 5, a random copolymer according to item 6 or of a crosslinked product according to item 7 or 8 for forming an adhesive tape or sheet, wound dressing or first aid dressing.

The aspects of the present invention will now be explained in more detail. In the following description, the terms are defined as follows:

The term "(meth)acrylate" or "(meth)acrylic acid" is used to denote commonly the corresponding acrylate and methacrylate. Thus, for instance, the term "(meth)acrylic acid" covers both methacrylic acid and acrylic acid, and the term "(meth)acrylate" covers both acrylates and methacrylates. The (meth)acrylate or the (meth)acrylic acid may consist only of the methacrylate or methacrylic acid, respectively, or may consist only of the acrylate or the acrylic acid, respectively, yet may also relate to a mixture of the respective acrylate and methacrylate (or acrylic acid and methacrylic acid).

The term "comprising" is used open-endedly, so that for instance a composition "comprising" certain components can also contain further components in addition to the specified components. Yet, the term "comprising" also denotes that the composition may consist of, or may essentially consist of, the recited components, so that the term also includes embodiments wherein the presence of further components than the ones specifically recited are excluded. In the case that the term "comprising" means "essentially consisting of", the allowed amount of other components than those specifically recited is low, typically less than 20%, preferably less than 10% and more preferably less than 5%, of the total amount of the component or composition that is described to "comprise" the recited components.

The term "pressure-sensitive adhesive" or "PSA" refers to a viscoelastic material that exhibits tackiness and adheres to a wide variety of substrates after applying only light pressure (e.g. finger pressure). A possible definition of pressure-sensitive adhesives is given by the Dahlquist criterion, which indicates that the materials have a storage modulus (G') of less than about $4.0*10^{-5}$ Pa (measured at room temperature).

The term "(meth)acrylate" relates to esters of acrylic acid or methacrylic acid with (preferably non-tertiary) alcohols, the alcohols preferably having between 2 and 14 carbon atoms, preferably between 2 and 8 carbon atoms, more preferably between 4 and 8 carbon atoms. In a preferred embodiment, the (meth)acrylate is represented by the following formula II:

wherein $R^3$ is hydrogen or a $CH_3$ group, and $R^4$ represents a hydrocarbon group having 1-14 carbon atoms, preferably a straight or branched alkyl group having 1 to 14, preferably 2 to 8 carbon atoms.

The term "(meth)acrylic monomer" is used to denote commonly both (meth)acrylates as defined above, as well as acrylic acid and methacrylic acid. The term "(meth)acrylic monomer" thus includes (meth)acrylates and (meth)acrylic acid.

The term "copolymer" denotes a polymer of any length (including oligomers) obtained by reacting 2, 3, 4 or more types of polymerizable monomers, and therefore includes terpolymers, tetrapolymers, etc. The polymers of the present invention, which are obtainable by reacting the polymerizable composition of the present invention, are random copolymers and are therefore different from block copolymers and mere blends of different homopolymers.

The term "hotmelt adhesive" is used interchangeably to denote the random copolymer obtainable by reacting the polymerizable composition of the present invention. The term "hotmelt adhesive composition" is used to denote a composition comprising or consisting essentially of the random copolymer and which contains typically less than up to e.g. 20% by weight, preferably less than 10% by weight, and further preferably less than 5% by weight of the total of the "hotmelt adhesive composition" of other components, such as a solvent.

The term "solvent-based adhesive composition" is used to denote a composition comprising (or consisting of) the random copolymer (which is obtainable by reacting the polymerizable composition of the present invention) and a solvent, wherein the amount of the solvent is greater than 20% by weight, further preferably greater than 40% by weight of the total of the solvent-based adhesive composition.

The term "crosslinked pressure-sensitive adhesive" is used to denote the crosslinked product obtainable by irradiating the hotmelt adhesive or the hotmelt adhesive composition with UV irradiation. The term "pressure sensitive adhesive" may be used interchangeably.

1. Polymerizable Composition

The polymerizable composition of the present invention contains at least (a) a polymerizable monomer of formula (I), (b) a copolymerizable UV-initiator, (c) at least one copolymerizable (meth)acrylic monomer, and optionally (d) at least one copolymerizable non-(meth)acrylic monomer.

(a) Polymerizable Monomer of Formula (I)

Formula (I) is given below:

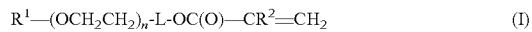

wherein $R^1$ is hydrogen or a $C_1$-$C_6$ alkyl group, n is an integer from 1 to 100, L is a single bond or a divalent linking group, preferably a single bond or a $C_{1-6}$ alkylene group, and $R^2$ is hydrogen or a $CH_3$ group.

The amount of the polymerizable monomer of formula (I) is between 2.5 and 40% by weight of the total of all polymerizable monomers (a), (b), (c) and (d). The presence of monomer of formula (I) in the specified amount of 2.5-40% by weight of the total of all polymerizable monomers (a), (b) (c) and (d) (if present) provides the final UV-crosslinked product with breathability, as required for applications in the medical field or personal care items, such as pressure-sensitive adhesives for plasters and wound dressings or athletic tapes.

The amount of the monomer of formula (I) in the polymerizable composition of the present invention is generally between 2.5 and 40% by weight of the total of all polymerizable monomers (a), (b), (c) and (d). Yet, the lower limit of the amount of the monomer of formula (I) can also be 3.0% by weight or higher, 4.0% by weight or higher or 5.0% by weight or higher. The upper limit of the content of the monomer of formula (I) is generally 40% by weight, preferably 30% by weight or 25% by weight or less, further preferably 20% by weight or less or 15% by weight or less, based on the total of all monomers (a), (b), (c) and (d).

Generally, a higher amount of the monomer of formula (I) leads to an increased breathability and water vapor permeability of the final UV-crosslinked pressure-sensitive adhesive, while a too high amount of the monomer of formula (I) leads to a reduced adhesion strength of the crosslinked pressure-sensitive adhesive. Therefore, preferably the amount of the monomer in the polymerizable composition is 5.0% or more by weight to 30% by weight or less, more preferably 8.0% by weight or more and 25.0% by weight or less, and further preferably 10.0% by weight or more to 25.0% by weight or less, based on the total of the polymerizable monomers (a), (b), (c) and (d) (if present).

In the monomer of formula (I), $R^2$ is preferably a $CH_3$ group, i.e. the monomer of formula (I) is preferably a methacrylate. Further, independently from the monomer being an acrylate or methacrylate, the ethylene oxide chain is preferably terminated by an alkyl group, i.e. $R^1$ is preferably a $C_1$-$C_6$ alkyl group. Further preferably, $R^1$ is a methyl group.

The variable n denotes the number of ethylene oxide groups and denotes an integer of 1 to 100. Preferably, n is 2 or higher, more preferably 5 or higher, and preferably 80 or less, more preferably 50 or less. Even more preferred are values of n between 5 and 45, further preferably between 5 and 30.

L represents a single bond or a linking group, preferably a single bond or a $C_1$-$C_6$ alkylene group. Possible examples of a divalent linking group represented by L other than a $C_1$-$C_6$ alkylene group include a divalent organic group having between 1 to 15 carbon atoms, between 2 to 30 hydrogen atoms and optionally including one, two or more heteroatoms selected from N, O and S, such as a di(alkylene) ether or di(alkylene)ester group, a di(alkylene)amino group, or a di(alkylene)thioether group. The linking group may be completely aliphatic (i.e. L does not include an aromatic ring), but may also contain an aromatic ring, such as a benzene ring or a pyridine ring. Further, the linking group represented by L may or may not contain an alicyclic ring.

Preferably, L is a single bond or a $C_1$-$C_6$ alkylene group. The $C_1$-$C_6$ alkylene group may be straight or branched, yet is preferably straight.

Monomers of formula (I) can be easily synthesized by a skilled person by reacting a poly(alkylene oxide) terminating with a hydroxyl group with (meth)acrylic acid, thereby forming the corresponding ester of formula (I). Further, compounds of formula (I) are commercially available, for instance as aqueous solution under the trade name "Bisomer", e.g. as 50% aqueous solution of methoxypolyethyleneglycol methacrylate, which is marketed under the trade name Bisomer S20W by Geo Specialty Chemicals. Also available are Visiomer MPEG 750 MA W, Visiomer MPEG 2005 MA W or Visiomer MPEG 5005 MA W (trade marks, all available from Evonik) or Norsocryl 402 or Norsocryl 405 (available from Arkema). The monomers can also be obtained in the form of a 100% dry product, like Bisomer MPEG 350 MA or Bisomer MPEG 550 MA (GEO Speciality Chemicals) or Allyl Alcohol ethoxylate like Rhodasurf AAE-10 E from Rhodia.

The molecular weight of the monomer of formula (I) is mainly determined by the value of the variable n, denoting the number of ethylene oxide groups. Preferably, the molecular weight of the monomer of formula (I) is between 200 and 3,000 g/mol, more preferably between 300 and 2,700 g/mol and further preferably between 350 and 1,500. By far preferably, the monomer of formula (I) is a methoxypolyethyleneglycol methacrylate having a number of repeating ethylene oxide groups corresponding to the preferred, further preferred or most preferred ranges of the variable n recited above (2-80, 5-50, or 5-30).

(b) Copolymerisable UV-Initiator

The compound (b) is a copolymerisable UV-initiator. This compound typically has a copolymerisable group, such as an ethylenically unsaturated group, and a moiety that is decomposable by UV-irradiation, thereby forming radicals upon irradiation with UV light. That is, upon application of UV-irradiation, the copolymerized units derived from compound (b) decompose and form radicals, which cause a three-dimensional crosslinking of the essentially linear, random copolymer formed in the solvent polymerization step, thereby forming the crosslinked pressure sensitive adhesive having breathability.

In one embodiment, the compound (b) is typically an ester of (meth) acrylic acid, such as an acetophenone or benzophenone derivative thereof. Such compounds are described, for instance, in EP 346734 A, EP 377199 A (claim 1), DE 4037079 A (claim 1) and DE 3844444 A (claim 1). The compound (b) can also be benzoin acrylate.

A preferred class of compounds of the copolymerizable UV-initiator is a copolymerizable (meth)acrylate having a UV-decomposable group, such as the compounds represented by the following formula (III):

$$X-OC(O)-CR^3=CH_2 \quad (III)$$

Herein, $R^3$ is hydrogen or a methyl group, and X represents a group comprising a UV-decomposable moiety, preferably including an acetophenone, benzophenone or benzoin group.

Preferably, the compound (b) has a phenyl ring that is linked to the remainder of the molecule via a linker group that easily decomposes under UV irradiation, such as a carbonate group. A carbonate group is a group of the following formula

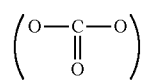

Further preferably, the compounds are represented by the following formula (IV) or (V), as described in EP 1 213 306 A2.

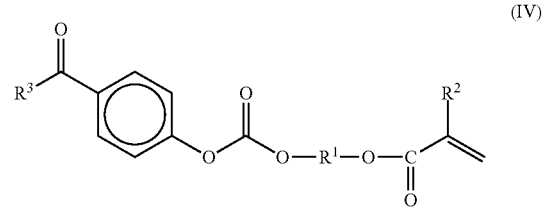

wherein $R^1$ represents an organic linker residue having between 1 and 30 carbon atoms, such as an alkylene group, an alkenylene group or a 5- or 6-membered cyclic aliphatic or aromatic group, each of which may be substituted or unsubstituted by a substituent selected from a straight-chain or branched alkyl group having 1-6 carbon atoms, an alkenyl group having 2-6 carbon atoms, a halogen atom (iodo, fluoro, chloro or bromo), a nitro group, a cyano group, an amino group, an amide group, an amino group, or a nitrile group; $R^2$ represent a hydrogen atom or a methyl group, and $R^3$ represents an optionally substituted phenyl group or a $C_1$-$C_6$ alkyl group.

Further preferably, $R^1$ represents an alkylene group, in particular a $C_1$-$C_8$ alkylene group. $R^3$ preferably represents a methyl group or a phenyl group, further preferably a phenyl group. Most preferably, $R^3$ represents a phenyl group and $R^1$ represents a $C_1$-$C_8$ alkylene group.

Further preferably a copolymerizable UV-initiator is represented by formula (V) below:

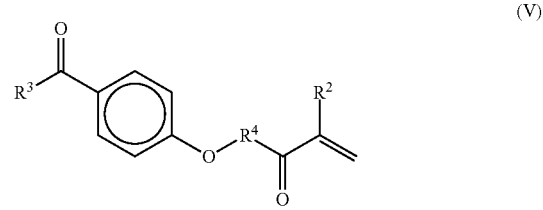

wherein $R^3$ and $R^2$ have the same meaning as defined above for formula (IV), and $R^4$ represents a single bond, a group $R^1$ as defined above for formula (IV), $(-CH_2-CH_2-O)_n$,

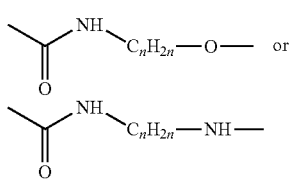

wherein in each case n represents an integer of 1-12.

Other preferred classes of the copolymerizable UV-initiator do not contain a carbonate group, but instead contain several phenyl rings that are linked via a carbonyl or an ether linkage. Preferable compounds within this class of copolymerizable UV-initiators are represented by formula (VI) below:

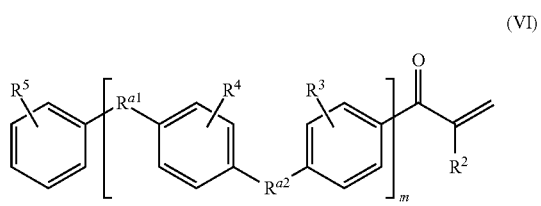

Herein, $R^2$ represents a hydrogen atom or a methyl group, preferably a methyl group, and $R^{a1}$ and $R^{a2}$, which may be the same or different, each represents a carbonyl group —C(O)— or an ether linkage —O—. Preferably, one of $R^{a1}$ and $R^{a2}$ represents a carbonyl group, and the other represents an ether linkage, and further preferably $R^{a1}$ represents a carbonyl group and $R^{a2}$ represents an ether linkage.

m represents an integer from 1 to 5, preferably an integer of 1 or 2, further preferably 1. $R^3$, $R^4$ and $R^5$ each represent one or two optional substituents, which are preferably selected from C1-6 alkyl groups, halogens (iodo, chloro, bromo or fluoro), amino groups, nitro groups, nitrile groups, and hydroxyl groups. However, preferably all of $R^3$, $R^4$ and $R^5$ are absent (i.e. are hydrogen atoms), and the benzene rings are unsubstituted. If m denotes an integer of 2 or greater, the several $R^{a1}$, $R^{a2}$, $R^3$ and $R^4$ may be the same or different.

A particular preferred compound of formula (VI) has the following structure:

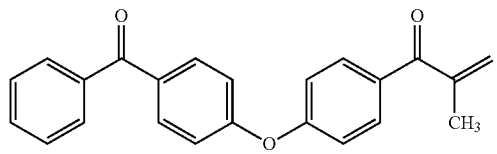 [SMILES: C=C(C)C(=O)c1ccc(Oc2ccc(C(=O)c3ccccc3)cc2)cc1]

While the mechanism by which the compounds generate radicals upon UV-irradiation is not fully understood, it is thought that a decomposition of the compound by cleavage of the bond between a carbonyl group and the benzene ring and/or the ether linkage between the phenyl groups occurs upon UV-irradiation, thereby forming benzyl radicals. Since the crosslinking efficiency of compounds of formula (VI) is generally higher than the crosslinking efficiency of benzophenone and acetophenone derivatives of formula (IV) and (V), the compounds of formula (VI) are preferred for use in the present invention.

The amount of the copolymerizable UV-initiator (b) in the polymerizable composition of the present invention needs to be sufficient to enable a sufficient crosslinking ability of the resulting essentially linear polymer upon UV-irradiation, yet should not be too high in order to avoid a deterioration of the adhesive or breathable properties of the final crosslinked pressure-sensitive adhesive. As such, the amount of the copolymerizable UV-initiator is typically 5% or less of all copolymerizable monomers (a), (b), (c) and (d) (if present), preferably 2% by weight or less, further preferably 1% by weight or less, even further preferably 0.5% by weight or less. Yet, the amount thereof may also be as low as 0.2% or less, in particular in cases where a lower crosslinking density may be sufficient for the intended purpose.

(c) Copolymerizable (Meth)Acrylic Monomer

In the polymerizable composition of the present invention, at least one copolymerizable (meth)acrylic monomer (c) is present in addition to (a) the polymerizable monomer of formula (I), which provides breathability to the pressure-sensitive adhesives, and (b) the copolymerizable UV-initiator, which allows the formation of a three-dimensional polymer network upon UV-irradiation and crosslinking of the initially formed hot-melt adhesive comprising mainly linear copolymer molecules.

The copolymerizable (meth)acrylic monomer (c) is the typical ingredient that is responsible for the pressure-sensitive adhesive properties of the resulting product. Typically, the copolymerizable (meth)acrylic monomer is selected from (meth)acrylic acid and (meth)acrylates ((meth)acrylic acid esters). The preferable (meth)acrylates are represented by the following formula

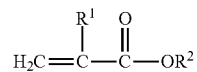

wherein $R^1$ is H or $CH_3$, and wherein $R^2$ is selected from linear or branched hydrocarbon groups, such as substituted or unsubstituted, linear or branched alkyl groups. The number of carbon atoms in $R^2$ is preferably between 1 and 10, further preferably between 4 and 8. Examples of suitable (meth)acrylates include, but are not limited to, methyl acrylate, ethyl acrylate, n-butyl acrylate, tert.-butyl acrylate, 2-ethylhexyl acrylate, 2-methylbutyl acrylate, 4-methyl-2-pentyl acrylate, ethoxy ethoxyethyl acrylate, hexyl acrylate, octyl acrylate, nonyl acrylate, isononyl acrylate, iseodecyl acrylate, decyl acrylate, lauryl acrylate, octyl acrylate, isooctyl acrylate.

Other suitable (meth)acrylic monomers are hydroxyethyl acrylate, hydroxyproyl acrylate and hydroxybutyl acrylate, acryl amide, acrylonitrile, ethyleneglycol diacrylate, allyl acrylate, and glycidyl acrylate.

Further, besides these (meth)acrylates, acrylic acid and methacrylic acid may be used, either alone, but preferably in combination with one or more (meth)acrylates.

The at least one copolymerizable (meth)acrylic monomer (c) may consist of only one of the above (meth)acrylates and (meth)acrylic acid, but typically more than one copolymerizable (meth)acrylic monomer is employed in the present invention. For instance, the copolymerizable (meth)acrylic monomer (c) may comprise 2, 3, 4 or 5, preferably 2, 3, or 4 different monomers selected from copolymerizable (meth) acrylate monomers and (meth)acrylic acid, which together constitute the copolymerizable (meth)acrylic monomer (c). For instance, the copolymerizable (meth)acrylate monomer (c) may be formed by three different species, such as 2-ethylhexyl acrylate, butyl acrylate and acrylic acid.

In a preferred embodiment A, the copolymerizable (meth) acrylic monomer (c) is formed by 60-80 by weight of 2-ethylhexyl acrylate, 10-30% by weight of butyl acrylate and 0-15% by weight of acrylic acid and/or methacrylic acid.

In another preferred embodiment B, the copolymerizable (meth)acrylic monomer (c) is formed by 70-90% by weight of butyl acrylate, 30%-10% by weight of 2-ethylhexyl acrylate, and 0%-20%, preferably 0%-10% by weight of acrylic acid and/or methacrylic acid.

The total amount of the at least one copolymerizable (meth)acrylic monomer forming the component (c) in the UV-curable composition, is preferably 65-95% by weight of the total of the components (a), (b), (c) and (d) (if present), further preferably 70-90 by weight, further preferably 74-85% by weight. In case that the copolymerizable (meth) acrylic monomer (c) is formed by more than one component, such in the above preferred embodiments A and B, the "total amount of the at least one copolymerizable (meth)acrylic monomer" relates to the total amount of all copolymerizable (meth)acrylic monomers.

(d) Further Copolymerizable Components

In addition to the components (a), (b) and (c), the polymerizable composition of the present invention may or may not further comprise additional copolymerizable monomers (d) that are non-acrylic and do not have a UV-decomposable group.

If present, such additional copolymerizable monomers (d) are typically present in an amount of 30% by weight or less, preferably 25% by mass or less, based on the total of the monomers (a), (b), (c) and (d). Since the presence of the copolymerizable monomer (d) is optional, it may also be absent, but if present its amount is typically more than 0.01% by weight, preferably 0.5% by weight or more, further preferably 1.0% by weight or more of the total of the monomers (a), (b), (c) and (d).

Such additional comonomers (d) may be employed to modify the properties of the resulting linear or crosslinked product and are typically selected from the group consisting of ethylenically unsaturated carboxylic acids other than (meth)acrylic acid and (meth)acrylates, ethylenically unsaturated phosphonic acids, ethylenically unsaturated sulphonic acids (such as itaconic acid, fumaric acid, crotonic acid, citraconic acid, maleic acid, styrene sulphonic acid, 2-acrylamido-2-methylpropane sulphonic acid, vinyl phosphonic acid and the like), (meth)acrylamides, vinyl esters, such as vinyl acetate, VEOVA 10, VEOVA 9 (from Momentive), and n-vinyl lactams. Other possible monomers (d) are styrene, maleic anhydride, and diallyl phthalate.

The most preferred comonomer (d) is vinyl acetate. Further preferably, the vinyl acetate is present in an amount of 10-25% by weight of the total of the monomers (a), (b), (c) and (d).

In the polymerizable composition of the present invention, the components (a), (b), (c) and (d) (if present) are distinct from other. Hence, for instance a given compound cannot at the same time be a component (a) and (c). This means that component (a) is different from components (b) and (c) (and (d), if present), component (b) is different from components (a) and (c) (and (d), if present), and component (c) is different from components (a) and (b) (and (d), if present).

(e) Solvent

The UV-curable composition of the present invention comprising the components (a), (b) and (c) and optionally (d) typically contains further (e) a solvent. This solvent is generally selected such that the components (a), (b), (c) and (d) (if present) can be reacted, e.g. by solvent polymerization, to prepare a substantially linear random copolymer comprising repeating units derived from the components (a), (b), (c) and optionally (d). The solvent is preferably selected from alcohols, aliphatic and aromatic hydrocarbons, ketones, esters and mixtures thereof. It is possible to use only a single solvent or a mixture of two or more solvents.

The solvent typically has a boiling point of less than 150° C. at 1 bar. Typical and preferable examples of solvents include methanol, ethanol, n-propanol, isopropanol, butanol, hexanol and other primary and secondary alcohols, acetates, such as methyl acetate, ethyl acetate, propyl acetate, isopropyl acetate, butyl acetate etc., acetone, methyl ethyl ketone, hydrocarbons, such as hexane, cyclohexane, heptane, and toluene, and mixtures thereof. Also used can be white spirits 60-95 like Exxsol DSP 60-95SH.

Preferred solvents are ethyl acetate, heptane, ethanol and isopropanol. Another preferred solvent is am mixture of ethyl acetate with another solvent miscible therewith, wherein the amount of ethyl acetate is less than 50% by weight and the remainder is made up from one or more other solvents, which are preferably not alkyl acetates or ketones. A preferred example of such a solvent system comprises 40 to less than 50% by weight of ethyl acetate and more than 50 to 60% by weight of heptane and/or ethanol (or isopropanol), such as 45% by weight ethyl acetate/55% by weight heptane or 45% by weight ethyl acetate/55% by weight ethanol (or isopropanol)

The amount of solvent is generally between about 30% to about 80% by weight, based on the totality of the components (a), (b), (c) and (d) and the solvent. In other words, the solvent typically makes up between 30 wt-% and 80 wt-% of the total of all components forming the polymerizable composition of the present invention.

(f) Thermal Polymerisation Initiator

According to the present invention, the components (a), (b) and (c) and optionally (d) are copolymerized, optionally in the presence of a solvent (e), to thereby form a random copolymer that is not three-dimensionally crosslinked, but rather consists of essentially linear or branched polymer chains having repeating units derived from the components (a), (b), (c) and optionally (d), which are distributed randomly along the polymer chain.

The formation of this random copolymer can be initiated by heating the respective components, typically in a solvent (e). However, in order to facilitate the reaction, typically a thermal polymerization initiator (f) is added in a catalytically active amount, such as less than 1% by weight of the total of all polymerizable monomers (a), (b), (c) and optionally (d).

Useful thermal polymerization initiators are known to the skilled person and can be identified without undue burden. Typical examples thereof include azo compounds, such as 2,2' Azobis (Isobutyronitrile) like Vazo 64 (Du Pont) or AZND (Atochem) or 2,2' azobis (2-methylbutyronitrile) like Vazo 67 (Du Pont), or peroxides, such as benzoyl peroxide like Perkadox L-W75 (Akzo Nobel) or Retic BP-W 25 (Oxido), or dilaurylperoxide like Laurox (Akzo Nobel) or Retic LP (Oxido), or tert-Butyl peroxy-2-ethylhexanoate like Trigonox 21S (Akzo Nobel or TBPEH (Degussa), or tert-Butyl peroxypivalate like Trigonox 25 C-75 (Akzo Nobel) or Percarbonates such as di(4-tert-butylcyclohexyl peroxydicarbonate) like Perkadox 16S (Akzo Nobel).

The nature of the thermal polymerization initiator is generally not crucial for the present invention, and any polymerization initiator can be used as long as a radical polymerization can be initiated.

(g) Further Additives

In addition to the components (a), (b), (c) and optionally (d) and/or (e), the polymerizable composition may further comprise (g) additives that do not form part of the polymer formed by polymerization of the components (a)-(c) and, if present, (d). Such additives can be suitably determined by the skilled person based on common knowledge in this field and include, for instance, chain transfer agents, tackifiers, plasticizers, pigments and dyes. However, preferably the polymerizable composition comprises only minor amounts, such as less than 2% by weight, of such further components. Exemptions to this rule are plasticizers and tackifiers, which may be included in an amount of up to 25% by weight of the polymerizable composition.

More preferably, the polymerizable composition consists of the components (a), (b), (c), optionally (d), and optionally the solvent (e) since then the desired random copolymer can be obtained by simple removal of the solvent, e.g. by evaporation.

Formation of the Random Copolymer

Typically, the random copolymer is prepared from the polymerizable composition of the present invention by reacting the components (a), (b), and (c), and (d) (if present). For this purpose, a reactor typically containing a solvent (e) and a radical polymerization initiator (f), such as the thermal polymerization initiator described above, is heated in the absence of any monomers (a) to (d), or in the presence of only a small amount of one or more thereof, to form radicals that initiate the copolymerization. Then, the monomers (a) to (d) or solutions thereof are fed to the polymerization reactor slowly over time, typically over several hours (e.g. 1-10 hours), to copolymerize the monomers (a), (b), (c) and (d) (if present).

The polymerization of the components can be performed as a continuous process, but is preferably performed as a batch process. The reaction container is typically a vessel equipped with a stirrer, a thermometer, a condenser, one ore more addition funnels and a temperature controller (such as heating). Further, the reaction is typically conducted under inert atmosphere such as nitrogen. A conversion of about 98%-99% is typically obtained in about 20 hours.

Subsequently to the reaction, typically the solvent is removed in order to obtain the random copolymer. This random copolymer may then also be referred to as hotmelt adhesive, since the viscosity of the random copolymer is greatly reduced upon heating, so that it can be processed further (e.g. by application on a backing or substrate). The weight-average molecular weight Mw of the random copolymer obtained by this polymerization process is typically in the range of 50,000 to 600,000 as measured by GPC using a polystyrene standard.

Crosslinking, Crosslinking Product and Composite Material Comprising the Cross-Linked Product As outlined above, the random copolymer obtained from the polymerizable composition after removal of the solvent is a hotmelt adhesive and can be used in the form of a hotmelt adhesive composition essentially consisting of the random copolymer. Alternatively, it can be used in the form of a solvent-based adhesive composition, comprising the random copolymer and further a solvent, as defined above. These hotmelt- or solvent-based adhesive compositions can be applied to a backing or a substrate, thereby forming the precursor of a composite material of the present invention. For this purpose, a variety of coating methods, including brush, roll, spray, spread, wire, gravure, transfer roll, air knife or doctor blade coating can be applied.

Typically, the applied random copolymer is essentially solvent-free at the stage of application to a substrate or backing, i.e. is in the form of a hotmelt adhesive composition wherein the solvent content is preferably 2% by weight or less, further preferably 1% by weight or less. The thickness of the layer of the random copolymer (hotmelt adhesive) may vary over a broad range of about 10 micrometer to several hundred micrometer and is preferably in the range of 10 micrometer to 100 micrometer, further preferably 10 micrometer to 50 micrometer. Put differently, the hotmelt adhesive is usually applied to a substrate or backing in a coating weight of between 2 and 300 $g/m^2$, preferably 12-100 $g/m^2$, and the desired coating weight can be determined by the skilled person in view of the intended purpose. For instance, adhesive labels typically have coating weights 12-18 $g/m^2$, and adhesive tapes and wound dressings typically have coating weights of 30-100 $g/m^2$ of the hotmelt adhesive (the random copolymer)

After the hotmelt adhesive (random copolymer) has been applied to a substrate or backing, the random copolymer is crosslinked by irradiation with UV-light. By this UV-irradiation, the moieties attached to the repeating units derived from the copolymerizable UV-initiator (b), which are typically distributed in random along the polymer chain, are decomposed, thereby forming radicals. These radicals are then believed to abstract hydrogen radicals from e.g. an alkyl residue of a repeating unit derived from, for instance, butyl acrylate. As well-known in the art, such a radical propagation and polymerization step is random, so that crosslinking connections between the polymer chains of different molecules of the random copolymer are formed, thereby forming a three-dimensional polymer network on the substrate or backing. By this crosslinking reaction, the viscoelastic properties of the material are shifted more towards the elastic side, and a better balance between adhesion and cohesion is obtained. Also, the required shear-resistance is obtained, and the viscosity of the material is increased. By this UV crosslinking, therefore a pressure sensitive adhesive having the required balance of properties is formed on the backing or substrate.

The UV-irradiation step can be performed under conditions that are well-known in the art. Typically, UV-irradiation at wavelength between 200 nm and 400 nm is used, and the UV intensity on the surface of the substrate carrying the layer of the random copolymer is typically within the range of 10-500 $mJ/cm^2$, preferably 20-100 $mJ/cm^2$.

By the UV-irradiation and the crosslinking caused thereby, the viscosity of the adhesive increases (i.e. the crosslinked product has a greater viscosity compared to the random copolymer prior to the UV-irradiation). Furthermore, due to the three-dimensional crosslinking, the solubility of the adhesive composition is reduced. Accordingly, the crosslinked adhesive after the UV-irradiation remains stable on a backing or substrate. Further, it is possible to provide only certain areas of the substrate or backing with a crosslinked adhesive by a patterned exposure with UV-light and following removal of the random copolymer from non-irradiated portions of the substrate or backing.

In addition, as already explained above, the application of the non-crosslinked random copolymer on the backing, followed by crosslinking via UV irradiation, allows processing the polymer in a relatively viscous state, in particular at higher temperatures, and then modifying the viscoelastic properties of the polymer by crosslinking towards a more elastic state, thereby obtaining optimum viscoelasticity and performance as pressure-sensitive adhesive.

The substrate or backing can be selected from a wide variety of materials. The backing or substrate may include one or more layers and may be in a variety of forms, such as films or foams. Examples of suitable backing include well-known materials, such as polyesters, polyurethanes, polyether block amides and porous or non-porous polyethylene films. Yet, in order to make the most benefit of the breathable properties of the crosslinked adhesive obtained after the UV-irradiation, the backing or substrate preferably has a great breathability as well and is therefore preferably selected from breathable films having a water vapor transmission rate of 250 g/m²×24 h or more, such as porous polyethylene or polyester. The production of such porous and/or breathable films is known in the art and can be achieved e.g. by stretching a film containing a porous filler, such as fatty-acid coated calcium carbonate.

If desired, it is also possible to provide a protective layer on the side of the adhesive of the composite material typically consisting of the crosslinked adhesive layer on the substrate, as explained above. This protective layer may then be made from a material known in the art, such as polyethylene, polypropylene, polyester or another plastic film. Such a protective film may be particularly desirable if the composite material takes the form of a first aid wound dressing (plaster) or the like, since it protects the layer of crosslinked pressure-sensitive adhesive from contamination prior to application onto the skin of a wearer.

Further, many dressings and sticking plasters use textile materials as backing. These can be selected from fabrics and nonwoven materials. These materials have mostly an open structure and thus provide virtually unlimited breathability, and therefore are also preferred embodiments of the backing in the present invention.

The present invention will be described in more detail by way of the following Examples, which are however not intended to limit the scope of the invention in any way.

EXAMPLES

Example A

Several vinyl-acrylic copolymers that are breathable and UV crosslinkable were prepared as described below:

Sample A was prepared as follows:

A monomer mixture containing as (meth)acrylic monomer (component (c)): 300 g of 2-ethylhexyl acrylate, 86 g of Butyl Acrylate, and 12.5 g of Acrylic Acid, as component (b): 1.5 g of a copolymerizable UV-initiator Visiomer 6976 (from Evonik), a 30% Solution of Benzophenone Methacrylate in Methyl Methacrylate/Methacrylic Acid, as component (a): 50 g of Bisomer MPEG 550 MA (a monomer providing breathability according to formula (I), a methoxy polyethyleneglycol methacrylate, average molecular weight 550 g/mol) and as component (d) 70 g of vinyl acetate;

was prepared in a glass vessel and stirred.

Thus, in this monomer mixture there is a total of 70 g of component (d), 399.55 g component (c), 0.45 g of component (b) and 50 g of component (a). In view of the total mass of 520 g of these monomers, this corresponds to 13.46% by weight of component (d), 76.83% by weight of component (c), 0.09% of component (b) and 9.62% of component (a).

A catalyst solution (also referred to as initiator solution in the following) was prepared by mixing 1 g of TBPEH (Tert-Butyl peroxy-2-ethylhexanoate) and 120 g of a mixture 55:45 of Heptane/Ethyl Acetate was prepared in a different vessel.

In a lab reactor (a 3 liter water jacketed reactor), an initial charge was prepared as follows: 200 g of a mixture 55:45 of Heptane/Ethyl Acetate, 130 g of the Monomer Mixture and 30.25 g of the catalyst solution were charged. This initial charge was stirred at 100 rpm and purged with nitrogen, then heated to reflux at 77-80° C. (the heating jacket was set to 92° C.). Around 7 minutes after reaching reflux, the heating jacket was set at 90° C. and the remainder of the monomer mixture and the catalyst solution were uniformly added into the reactor over 2.5 hours (the internal temperature of the reactor was around 80-85° C.)

At the end of the addition, the monomer tank was washed with 20 g of a mixture 55:45 of Heptane/Ethyl Acetate and added into the reactor, then the reactor was held at reflux for 1 hour.

3.5 hours after the start of the feeding, the residual monomers were scavenged with a initiator solution of 1 g of TBPEH and 60 g of a mixture 55:45 of Heptane/Ethyl Acetate. The jacket was set down to 88° C. and the scavenger solution was added for 1 h at constant rate. At the end of the addition, the tank was finally washed with 20 g of a mixture 55:45 of Heptane/Ethyl Acetate, and the reactor was held at reflux for other 3.0 hours (with the internal temperature between 77 and 80° C.), maintaining the jacket at 88° C.

Finally, 7.5 hours after the start of the feeding of the monomer mixture the reactor content was cooled and diluted with 58 g of a mixture 55:45 of Heptane/Ethyl Acetate.

The final product obtained has a solid content of 51.9% and a Viscosity of 3620 mPa*s.

The product can be used as solvent-based adhesive composition or can be dried (by removing the solvent) to obtain a hotmelt adhesive composition. The results are summarized in Table 2.

The results in table 2 relate to the material after solvent evaporation and application on a substrate (PET 36 microns film) with a coating weight of 30 g/m², and then crosslinking with a UV lamp emitting UV-C irradiation at an intensity of 30 mJ/cm².

Examples B-E

Further Examples were prepared as outlined above for Example A, mainly varying the amount of the breathable monomer (a) of formula (I) as recited in Table 1. The amount of the other monomers (c) and (d) were reduced to maintain the same total monomer quantity. In the Examples with high quantity of breathable monomer (a), also the initial solvent quantity was increased in order to maintain a similar viscosity.

In the tables, the following abbreviations are used:
2-EHA=2-Ethyl Hexyl Acrylate
AB=Butyl Acrylate
AM=Methyl Acrylate
AVM=Vinyl Acetate Monomer
AA=Acrylic Acid
UV Mon—1=Visiomer™ 6976 (a 30% Solution of Benzophenone Methacrylate in Methyl Methacrylate/Methacrylic Acid)
UV Mon—2=Esacure™ BHM (4-benzoyl-4'-(2-methylpropenoyl)-diphenyl ether)

Breath Mon 1—=Bisomer™ MPEG 550 MA (a methoxy polyethyleneglycol methacrylate, average molecular weight 550 g/mol)

Breath Mon 2—=Bisomer™ MPEG 350 MA (a methoxy polyethyleneglycol methacrylate, average molecular weight 350 g/mol)

Breath Mon 3—=Bisomer™ S 20 W (a 50% water solution of Bisomer MPEG 2000MA; a methoxy polyethyleneglycol methacrylate, average molecular weight 2080 g/mol Breath Mon 4—=Rhodasurf™ AAE/10-E, an allyl alcohol ethoxylate with ethoxy chains of around 10 moles from Rhodia TBPEH=Tert-Butyl peroxy-2-ethylhexanoate from Degussa Vazo 64™=2,2'-azobis-(2-isobutyronitrile) from DuPont Laurox™=dilauryl peroxide (Akzo Chemical)

Solv Mix—1=Solvent Mixture: 55% Heptane+45% Ethyl Acetate

Solv Mix—2=Solvent Mixture: 55% Ethanol+45% Ethyl Acetate

Exxsol™ DSP 60/95 SH=a dearomatized hydrocarbon fluid, mainly a mixture of Hexane(s) and Heptane(s) isomers with a low level of n-Hexane In the following tables, values in brackets ( ) indicate that the respective amount of the respective component relates to a composition defined previously, and are hence disregarded for the calculation of the total amount. For instance, the value of (130) for the Monomer mixture in the section "Initial Charge" denotes the amount of 130 g of the Monomer mixture defined at the top of the table (consisting e.g. for Ex. A of 300 g 2-EHA, 86 g AB, 70 g AVM, 12.5 g AA, 1.5 g UV Mon—1, and 50 g Breath Mon—1).

TABLE 1

| Components (g) | Examples A to E | | | | |
|---|---|---|---|---|---|
| | Ex. A | Ex. B | Ex. C | Ex. D | Ex. E |
| Monomer Mixture | | | | | |
| 2-EHA | 300.0 | 320.0 | 315.0 | 275.0 | 250.0 |
| AB | 86.0 | 86.0 | 86.0 | 86.0 | 76.0 |
| AVM | 70.0 | 100.0 | 80.0 | 45.0 | 30.0 |
| AA | 12.5 | 12.5 | 12.5 | 12.5 | 12.5 |
| UV Mon - 1 | 1.5 | 1.5 | 1.5 | 1.5 | 1.5 |
| Breath Mon - 1 | 50.0 | — | 25.0 | 100.0 | 150.0 |
| Initiator solution | | | | | |
| TBPEH | 1.0 | 1.0 | 1.0 | 1.0 | 1.0 |
| Solv Mix - 1 | 120.0 | 120.0 | 120.0 | 120.0 | 120.0 |
| Initial Charge | | | | | |
| Solv Mix - 1 | 200.0 | 200.0 | 200.0 | 250.0 | 290.5 |
| Mon Mixture | (130) | (130) | (130) | (130) | (130) |
| Initiator solution | (30.25) | (30.25) | (30.25) | (30.25) | (30.25) |
| Washing Mon Tank | | | | | |
| Solv Mix - 1 Scavengers | 20.0 | 20.0 | 20.0 | 20.0 | 20.0 |
| TBPEH | 1.0 | 1.0 | 1.0 | 1.0 | 1.0 |
| Solv Mix - 1 | 60.0 | 60.0 | 60.0 | 60.0 | 60.0 |

TABLE 1-continued

| Components (g) | Examples A to E | | | | |
|---|---|---|---|---|---|
| | Ex. A | Ex. B | Ex. C | Ex. D | Ex. E |
| Wash Ini Tank | | | | | |
| Solv Mix 2 Dilution | 20.0 | 20.0 | 20.0 | 20.0 | 20.0 |
| Solv Mix - 1 | 58.0 | 78.0 | 58.0 | 8.0 | 37.5 |
| Total | 1000 | 1020 | 1000 | 1000 | 1070 |

The final products (without removal of the solvents) were analyzed to determine:

(a) the analytical properties: solid content, viscosity of the liquid product, and Molecular Weight (measures by GPC (Gel Permeation Chromatography) in THF using a Polystyrene internal standard (b) the adhesive performances of an adhesive film (with a coating weight of 30 g/m$^2$), obtained by evaporating the solvent, coating the copolymer on a PET 36 microns film and then crosslinking with a UV lamp with UV-C of 30 mJ/cm$^2$.

(c) the MVTR, following UNI 4818-26

Table 2 summarizes the results. Herein:

"A" means adhesive failure on a stainless steel surface.

"D" means disanchorage failure of the adhesive on Polyester surface.

"C" means cohesive failure (the adhesive remains on both surfaces (polyester and stainless steel)).

The viscosity was measured using a Brookfield Mod RVT at 25° C. at 20 rpm. The solids content was determined by putting the product for 1 hour at 130° C. into a ventilated oven. The Peel Adhesion)(180° on stainless steel (ss) was measured according to FINAT Test Method (FTM1) at a dwell time of 20 minutes. The shear value was measured according to FTM8 at room temperature, using a weight of 1 kg at controlled surface areas of 1 square inch ((1")$^2$) and ½ square inch ((½")$^2$. The loop tack (=QS ss) was measured according to FTM9 on stainless steel. MVTR was measured according to UNI 4818-26.

TABLE 2

Examples A to E: Analysis

|  | UM | Ex. A | Ex. B | Ex. C | Ex. D | Ex. E |
|---|---|---|---|---|---|---|
| Analytical data |  |  |  |  |  |  |
| Solid Content | wt.-% | 51.9 | 50.4 | 51.3 | 52.0 | 48.6 |
| Viscosity | Mpa · s | 3620 | 3010 | 2600 | 4220 | 1920 |
| Mn |  | 41350 | 84000 | 68700 | 29000 | 22000 |
| Mw |  | 190000 | 312000 | 273000 | 55000 | 50100 |
| Adhesive Performance |  |  |  |  |  |  |
| Peel ss 20 min | G/25 mm | 800 | 1320 | 1130 | 300 | 200 |
| QS ss | G/25 mm | 810 | 1040 | 1150 | 500 | 370 |
| Shear ((½")$^2$ | min | 160D | 660C/D | 300C/D | 70A | 20A |
| Shear (1")2 | h | >100 | >100 | >100 | >100 | >100 |
| Breathability |  |  |  |  |  |  |
| MVTR | g/m$^2$ 24 h | 375 | 250 | 265 | 500 | 650 |

It is clear to see the influence of the quantity of the breathable monomer (a), i.e. the monomer of formula (I), on the MVTR. Increasing the quantity (% of total monomer quantity) leads to a significant increase of the MVTR of the adhesive film, as summarized in Table 2a below:

TABLE 2a

Examples A to E: MVTR vs % of Monomer (a)

|  |  | Example |  |  |  |  |
|---|---|---|---|---|---|---|
|  |  | B | C | A | D | E |
| Monomer (a) | Wt.-% of all monmers | — | 4.8 | 9.6 | 19.2 | 28.8 |
| MVTR | a/m$^2$ 24 h | 250 | 265 | 375 | 500 | 650 |

The quantity of the monomer (a) also has influence on the adhesive performances of the film: increasing the amount thereof leads to a reduction of the Peel strength of the film, a slight reduction of the Quick Stick (Loop Tack), while the influence on the shear value is less evident due to the high level of the UV monomer and the high crosslinking in the film.

Examples F-M

A second series of examples were prepared using a pure acrylic polymer (i.e. monomer (d) is absent). Table 3 summarizes the compositions.

The procedure is similar to the first series of Examples A-E, the differences being as follows:
- the waiting time after the start of the reaction was increased to 30 min;
- the feeding time was reduced to 90 min;
- the scavenger addition time reduced to 45 min;
- total reaction time (from start of the monomer addition, including delay and cooling) was reduced to 6 h 15 min.

Further, a different solvent mixture was used (Solv Mix—2) consisting of 55% by weight of ethanol and 45% by weight of ethyl acetate.

Examples F-M relate to a pure acrylic polymer. Also, the UV copolymerizable photoinitiator was different, and a comparison of two different breathable monomers (a) is made to evaluate the influence of the quantity and nature (in particular ethoxy chain length) of the breathable monomer (a) on the properties of the product and the dried adhesive film.

The following components were used:
Breath Mon 1—=Bisomer MPEG 550 MA (ethoxy chain around 10 EO moles)
Breath Mon 2—=Bisomer MPEG 350 MA (ethoxy chain around 6 EO moles)

To maintain the same total monomer quantity, the quantity of the acrylic momomers 2-EHA and AM were reduced, as shown in Table 3.

TABLE 3

Examples F to M

| Components (g) | Ex. F | Ex. G | Ex. H | Ex. I | Ex. L | Ex. M |
|---|---|---|---|---|---|---|
| Mon Mixture |  |  |  |  |  |  |
| 2-EHA | 323.0 | 323.7 | 283.0 | 283.0 | 248.0 | 248.0 |
| AM | 150.0 | 150.0 | 140.0 | 140.0 | 125.0 | 125.0 |
| AA | 25.0 | 25.0 | 25.0 | 25.0 | 25.0 | 25.0 |
| UV Mon - 2 | 2.0 | 1.3 | 2.0 | 2.0 | 2.0 | 2.0 |
| Breath Mon - 2 | — | — | 50.0 | — | 100.0 | — |
| Breath Mon - 1 | — | — | — | 50.0 | — | 100.0 |
| Initiator Sol. |  |  |  |  |  |  |
| TBPEH | 0.8 | 0.8 | 0.8 | 0.8 | 0.8 | 0.8 |
| Solv Mix - 2 | 140.0 | 140.0 | 140.0 | 140.0 | 140.0 | 140.0 |
| Initial Charge |  |  |  |  |  |  |
| Solv Mix - 2 | 80.0 | 80.0 | 80.0 | 80.0 | 80.0 | 80.0 |
| Mon Mixture | (250.0) | (250.0) | (250.0) | (250.0) | (250.0) | (250.0) |
| Initiator Sol. | (70.4) | (70.4) | (70.4) | (70.4) | (70.4) | (70.4) |
| Wash Mon Tank |  |  |  |  |  |  |
| Solv-Mix 2 Scavengers | 50.0 | 50.0 | 50.0 | 50.0 | 50.0 | 50.0 |
| TBPEH | 0.7 | 0.7 | 0.7 | 0.7 | 0.7 | 0.7 |
| Solv Mix - 2 | 40.0 | 40.0 | 40.0 | 40.0 | 40.0 | 40.0 |
| Wash Ini Tank |  |  |  |  |  |  |
| Solv Mix 2 Dilution | 20.0 | 20.0 | 20.0 | 20.0 | 20.0 | 20.0 |
| Solv Mix 2 | 148.5 | 148.5 | 148.5 | 148.5 | 148.5 | 148.5 |
| Total | 980 | 980 | 980 | 980 | 980 | 980 |

In table 4 are collected the analysis of the lab trials.

TABLE 4

| Examples F to M: Analysis | | | | | | | |
|---|---|---|---|---|---|---|---|
| | | Ex. F | Ex. G | Ex. H | Ex. I | Ex. L | Ex. M |
| Analytical data | | | | | | | |
| Solid Content | % | 52.2 | 52.0 | 51.6 | 51.1 | 50.7 | 51.0 |
| Viscosity | MPa s | 1450 | 1440 | 1570 | 1590 | 2350 | 1975 |
| Adhesive Performance | | | | | | | |
| Peel ss 20 min | G/25 mm | 1500 | 1850 | 1075 | 1120 | 825 | 650 |
| QS ss | G/25 mm | 1450 | 1570 | 1220 | 1095 | 825 | 720 |
| Shear (½")² | min | 2200A | 100C | 960A | 900A | 130A | 80A |
| Shear (1")² | h | >100 | 8.5C | >100 | >100 | >100 | >100 |
| Breathability | | | | | | | |
| MVTR | G/sm 24 h | 180 | 190 | 270 | 290 | 370 | 440 |

From this table it is derived that:
- as for the first series of experiments, increasing the quantity of monomer (a) increases the MVTR and reduces the adhesive performances of the film;
- Breath Mon—1, having a slightly longer EO chain than Breath Mon—2, has a bigger influence on the MVTR of the film, especially for high level of the monomer, see Table 4A.

TABLE 4A

| Examples F to M: MVTR on Breath Mon 1 and 2% | | | | |
|---|---|---|---|---|
| | | Example | | |
| | | F | H | L |
| Breath Mon - 2 | % of Monom | — | 10.0 | 20.0 |
| MVTR | g/m² 24 h | 180 | 270 | 370 |
| | | Example | | |
| | | F | I | M |
| Breath Mon - 1 | % on Monom | — | 10.0 | 20.0 |
| MVTR | g/m² 24 h | 180 | 290 | 440 |

Examples N-P

A third series of examples was made by introducing a new breathable monomer, Bisomer S 20 W from GEO Chemical. It is a copolymerizable monomer with a very long EO chain (around 43 moles), supplied as a 50% solution in water. The values in Table 5 relate to the amount of solution. The reaction procedure is the same as used in Examples A to E, except for the following: The solvent used was Ethyl Acetate, and the initiator used was Vazo 64.

TABLE 5

| Examples N to P | | | |
|---|---|---|---|
| Components (g) | Ex. N | Ex. O | Ex. P |
| Mon Mixture | | | |
| 2-EHA | 391.2 | 378.7 | 365.9 |
| AB | 92.7 | 80.2 | 68.0 |
| AA | 13.6 | 13.6 | 13.6 |
| UV Mon - 1 | 2.5 | 2.5 | 2.5 |
| Breath Mon - 3 | — | 25.0 | 50.0 |
| Initiator Sol. | | | |
| Vazo 64 | 1.0 | 1.5 | 2.0 |
| Ethyl Acetate | 99.0 | 98.5 | 98.0 |
| Initial Charge | | | |
| Ethyl Acetate | 100.0 | 150.0 | 220 |
| Mon Mixture | (125.0) | (125.0) | (125.0) |
| Initiator Sol. | (25.0) | (25.0) | (25.0) |
| Washing Mon Tank | | | |
| Ethyl Acetate | 70.0 | 30.0 | 40.0 |
| Scavengers | | | |
| Vazo 64 | 0.8 | 0.8 | 0.8 |
| Ethyl Acetate | 49.2 | 49.2 | 49.2 |
| Washing Init. Tank | | | |
| Ethyl Acetate | 20.0 | 20.0 | 20.0 |
| Dilution | | | |
| Ethyl Acetate | 160.0 | 150.0 | 70.0 |
| Total | 1000 | 1000 | 1000 |

Table 6 summarizes the properties of the materials obtained. It is derived that
- long EO chains have a big influence on the MVTR properties of the film: a quantity of around 5% of the breathable monomer (a) is enough to give an MVTR of 360 g/m²×24 h;
- the long EO chain and the water content influence the viscosity of the product.

TABLE 6

| Examples F to M: Analysis | | | | |
|---|---|---|---|---|
| | | Ex. N | Ex. O | Ex. P |
| Analytical data | | | | |
| Solid Content | % | 50.0 | 49.1 | 47.4 |
| Viscosity | MPa s | 2000 | 2200 | 4000 |

TABLE 6-continued

Examples F to M: Analysis

|  |  | Ex. N | Ex. O | Ex. P |
|---|---|---|---|---|
| Adhesive Performance |  |  |  |  |
| Peel ss 20 min | G/25 mm | 580 | 420 | 370 |
| QS ss | G/25 mm | 670 | 680 | 750 |
| Shear (½")$^2$ | min | 200 A | 180 A | 300 A |
| Shear (1")$^2$ | h | >100 | >100 | >100 |
| Breathability |  |  |  |  |
| MVTR | g/m$^2$ 24 h | 215 | 260 | 360 |

Table 6a demonstrates the influence of the monomer (a) on the breathability properties of the resulting film:

TABLE 6A

Examples N to P: MVTR vs amount of Breathable Monomer 3%

|  |  | Example | | |
|---|---|---|---|---|
|  |  | N | O | P |
| Breath Mon - 3 | % of Monom | — | 2.6 | 5.2 |
| MVTR | g/m$^2$ × 24 h | 215 | 260 | 360 |

Examples Q-T

A fourth series of examples was prepared using a pure acrylate polymer (i.e. monomer (d) is absent) to investigate, in a simple monomer composition system (Butyl Acrylate and Acrylic Acid), the influence of a an amount of a monomer (a) like Bisomer MPEG 350 MA for very high level (up to 40%) of the total monomer composition.

The procedure is similar to the first series of examples A-F, the differences are in the timing:

feeding time reduced to 135 min;

scavenger addition reduced to 45 min;

post-reaction time after scavenger addition was reduced to 150 min;

total reaction time (from start of monomer delay until cooling) reduced to 6 h 30 min.

Table 7 summarizes the compositions of the Examples, the only differences being in the monomer quantity of component (a), which is compensated for by the amount of butyl acrylate. The solvent was Ethyl acetate and the initiator was Vazo 64.

TABLE 7

Examples Q to T

| Components (g) | Ex. Q | Ex. R | Ex. S | Ex. T |
|---|---|---|---|---|
| Mon Mixture |  |  |  |  |
| AB | 473.5 | 373.5 | 323.5 | 273.5 |
| AA | 25.0 | 25.0 | 25.0 | 25.0 |
| UV Mon - 1 | 1.5 | 1.5 | 1.5 | 1.5 |
| Breath Mon - 2 | — | 100.0 | 150.0 | 200.0 |
| Ethyl Acetate | 50.0 | 50.0 | 50.0 | 50.0 |
| Initiator Sol. |  |  |  |  |
| Vazo 64 | 2.0 | 2.0 | 2.0 | 2.0 |
| Ethyl Acetate | 48.0 | 48.0 | 48.0 | 48.0 |

TABLE 7-continued

Examples Q to T

| Components (g) | Ex. Q | Ex. R | Ex. S | Ex. T |
|---|---|---|---|---|
| Initial Charge |  |  |  |  |
| Ethyl Acetate | 200.0 | 200.0 | 200.0 | 200.0 |
| Mon Mixture | (165.0) | (165.0) | (165.0) | (165.0) |
| Initiator Sol. | (15.0) | (15.0) | (15.0) | (15.0) |
| Washing Mon Tank |  |  |  |  |
| Ethyl Acetate | 20.0 | 20.0 | 20.0 | 20.0 |
| Scavengers |  |  |  |  |
| Vazo 64 | 0.7 | 0.7 | 0.7 | 0.7 |
| Ethyl Acetate | 49.3 | 49.3 | 49.3 | 49.3 |
| Washing Ini Tank |  |  |  |  |
| Ethyl Acetate | 20.0 | 20.0 | 20.0 | 20.0 |
| Dilution |  |  |  |  |
| Ethyl Acetate | 110.0 | 110.0 | 110.0 | 110.0 |
| Total | 1000.0 | 1000.0 | 1000.0 | 1000.0 |

Table 8 summarizes the analytical results of these examples.

TABLE 8

Examples Q to T: Analysis

|  | UM | Ex. Q | Ex. R | Ex. S | Ex. T |
|---|---|---|---|---|---|
| Analytical data |  |  |  |  |  |
| Solid Content | wt.-% | 51.4 | 51.0 | 51.2 | 51.3 |
| Viscosity | MPa s | 2350 | 4050 | 6070 | 6300 |
| Adhesive Performance |  |  |  |  |  |
| Peel ss 20 min | G/25 mm | 2820 Tr | 990 Tr | 780 | 340 |
| QS ss | G/25 mm | 1740 | 1070 | 930 | 580 |
| Shear (½")$^2$ | min | 170 A | 210 A | 110 A | 45 A/D |
| Shear (1")$^2$ | h | >100 | >100 | >100 | >100 |
| Breathability |  |  |  |  |  |
| MVTR | g/m2 24 h | 255 | 420 | 550 | 650 |

Also in this case is clear to see the influence of the quantity of the breathable monomer (a), i.e. Breath Mon—2, on the MVTR.

Increasing the Breath Mon—2 quantity leads to a significant increase of the MVTR of the adhesive film. A very high quantity of the breathable monomer (a) leads to a very high breathability of the polymer; this behavior is summarized in table 8A:

TABLE 8A

Examples Q to T: MVTR vs amount of Breath Mon 2

|  |  | Example | | | |
|---|---|---|---|---|---|
|  |  | Q | R | S | T |
| Breath Mon - 2 | % of Monomers | — | 20.0 | 30.0 | 40.0 |
| MVTR | g/m$^2$ × 24 h | 255 | 420 | 550 | 650 |

As demonstrated in the previous examples, the quantity of the monomer (a) also influences the adhesive performance of the film: an increase leads to a reduction of the Peel strength of the film and a slightly smaller reduction of the Quick Stick (Loop Tack).

The amount of monomer (a) also influences the viscosity of the product: without changing the amount of the other components, an increase in the amount of monomer (a) leads to an increase of the viscosity of the liquid product.

Examples U-Z

A fifth series of examples were prepared using a pure acrylate polymer (i.e. monomer (d) is absent); to check, in a simple monomer composition system (2-Ethyl-Hexyl Acrylate and Acrylic Acid) the influence of a different monomer (a) like Rhodasurf AAE/10-E (from Rhodia).

Different is also the used solvent: Exxsol DSP 60/95 SH=a dearomatized hydrocarbon fluid, which is a mixture of Hexanes and Heptane isomers with a low level of n-Hexane The procedure is similar to the first series of examples, the differences are in the timing:

feeding time was reduced to 120 min;

scavenger addition was reduced to 45 min;

post-reaction time after scavenger addition was reduced to 150 min;

total reaction time (from monomer delay start to cooling) was reduced to 6 h 15 min.

The initiator were: TBPEH and Laurox (dilauryl peroxide from Akzo).

Table 9 summarizes the compositions of Examples U to Z.

TABLE 9

| Examples U to Z | | | |
|---|---|---|---|
| Components | Ex. U | Ex. V | Ex. Z |
| Mon Mixture | | | |
| 2-EHA | 473.0 | 423.0 | 373.0 |
| AA | 25.0 | 25.0 | 25.0 |
| UV Mon - 1 | 2.0 | 2.0 | 2.0 |
| Breath Mon - 4 | — | 50.0 | 100.0 |
| Exxsol DSP 60/95 SH | 50.0 | 50.0 | 50.0 |
| Initiator Sol. | | | |
| TBPEH | 2.7 | 1.5 | 0.7 |
| Exxsol DSP 60/95 SH | 47.3 | 48.5 | 49.3 |
| Initial Charge | | | |
| Exxsol DSP 60/95 SH | 270.0 | 150.0 | 70.0 |
| Mon mixture | (220.0) | (220.0) | (220.0) |
| Initiator Sol. | (20.0) | (20.0) | (20.0) |
| Washing Mon Tank | | | |
| Exxsol DSP 60/95 SH | 40.0 | 40.0 | 40.0 |
| Scavengers | | | |
| Laurox | 0.5 | 0.5 | 0.5 |
| Exxsol DSP 60/95 SH | 49.5 | 49.5 | 49.5 |
| Washing Ini Tank | | | |
| Exxsol DSP 60/95 SH | 20.0 | 20.0 | 20.0 |
| Dilution | | | |
| Exxsol DSP 60/95 SH | — | 120.0 | 200.0 |
| Total | 980.0 | 980.0 | 980.0 |

Table 10 summarizes the analytical results of these Examples.

TABLE 10

| Examples U to Z: Analysis | | | | |
|---|---|---|---|---|
| | UM | Ex. U | Ex. V | Ex. Z |
| Analytical data | | | | |
| Solid Content | wt.-% | 52.5 | 52.6 | 51.6 |
| Viscosity | MPa s | 22700 | 2020 | 850 |
| Adhesive Performance | | | | |
| Peel ss 20 min | G/25 mm | 2250 Tr | 970 Tr | 130 Tr |
| QS ss | G/25 mm | 1310 | 1100 Tr | 500 Tr |
| Shear (1")² | min | 5 | 1 | 0.05 |
| Transpirancy | | | | |
| MVTR | g/m2 24 h | 200 | 350 | 450 |

Also in this case, it is clear to see the influence of the quantity of the breathable monomer (a), i.e. Breath Mon—4, on the MVTR.

Increasing the Breath Mon—4 quantity (% on tot monomer quantity) leads to a significant increase of the MVTR of the adhesive film. This is summarized in table 10 A:

TABLE 10A

| Examples U to Z: MVTR on Breath Mon 4% (on monomers) | | | | |
|---|---|---|---|---|
| | | Example | | |
| | | U | V | Z |
| Breath Mon - 4 | % on Monom | — | 10.0 | 20.0 |
| MVTR | a/m2 24 h | 200 | 350 | 450 |

As seen in the previous examples, the quantity of the monomer (a) also influences the adhesive performance of the film: increasing the Breath Mon—4 quantity correlates with a reduction of the adhesive properties of the film.

It is also clear that the amount of the breathable monomer (a) influences the viscosity of the product, since increasing the Breath Mon 4 quantity leads to a strong reduction of the molecular weight of the polymer.

The invention claimed is:

1. A polymerizable composition, comprising
   (a) a polymerizable monomer of formula (I),
   (b) a copolymerizable UV-initiator comprising an ethylenically unsaturated group,
   (c) at least one copolymerizable (meth)acrylic monomer, $$R^1\text{—}(OCH_2CH_2)n\text{-}L\text{-}OC(O)\text{—}CR^2\text{=}CH_2 \quad \text{Formula (I):}$$

wherein $R^1$ is hydrogen or a $C_1$-$C_6$ alkyl group, n is an integer from 2 to 100, L is a single bond or a divalent linking group, preferably a single bond or a $C_{1-6}$ alkylene group, and $R^2$ is hydrogen or a $CH_3$ group; and
   optionally (d) at least one copolymerizable non-acrylate monomer;
wherein the amount of the polymerizable monomer of formula (I) is between 2.5 and 40% by weight of the total of all polymerizable monomers (a), (b), (c) and (d); and
wherein the copolymerizable UV-initiator is selected from the group consisting of benzophenon(meth)acrylate, benzoin(meth)acrylate and compounds represented by formula (VI) below:

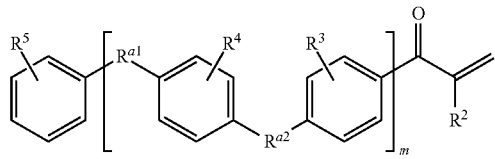

(VI)

wherein R² represents a hydrogen atom or a methyl group, preferably a methyl group, $R^{a1}$ and $R^{a2}$, which may be the same or different, each represents a carbonyl group —C(O)— or an ether linkage —O—; m represents an integer from 1 to 5, preferably an integer of 1 or 2, further preferably 1; $R^3$, $R^4$, and $R^5$, which may be the same or different, each represent one or two optional substituents, which are preferably selected from $C_{1-6}$ alkyl groups, halogens (iodo, chloro, bromo or fluoro), amino groups, nitro groups, nitrile groups, and hydroxyl groups, and if m is an integer of 2 or greater, the m $R^{a1}$, $R^{a2}$, $R^3$ and $R^4$ may respectively be the same or different.

2. The polymerizable composition according to claim 1, which further comprises (e) a solvent selected from alcohols, ethers, ketones, aliphatic and aromatic hydrocarbons, esters and mixtures thereof.

3. The polymerizable composition according to claim 1, wherein the copolymerizable UV- initiator is a compound having an acrylate or methacrylate moiety and a moiety that is decomposed by UV radiation to form radicals.

4. The polymerizable composition according to claim 1 wherein the at least one copolymerizable (meth)acrylic monomer (c) comprises (meth)acrylic acid, butyl (meth) acrylate and/or 2-ethylhexyl methacrylate.

5. A random copolymer obtainable by polymerizing a composition according to claim 1.

6. A hotmelt adhesive composition or a solvent-based adhesive composition comprising the random copolymer according to claim 5 and a solvent.

7. A crosslinked product obtainable by irradiating the random copolymer according to claim 5.

8. The crosslinked product according to claim 7, which has a moisture vapor transmission rate (breathability), MVTR, of at least 250 g/m² ×24 h according to UNI4818-26 at a coating weight of 30g/m².

9. A composite material comprising the crosslinked product according to claim 7 on a substrate.

10. The composite material according to claim 9, which is in the form of an adhesive sheet or tape, wound dressing, or plaster.

11. A method for forming an adhesive composite material, comprising the steps
   i. applying the random copolymer according to claim 5 preferably at a temperature of 120 - 160 ° C., onto a substrate; and
   ii. then irradiating the random copolymer or the hot melt or solvent-based composition with UV irradiation so as to crosslink the copolymer.

12. A method comprising applying the polymerizable composition according to claim 1 to a substrate to form an adhesive tape or sheet, wound dressing or first aid dressing.

* * * * *